United States Patent
Buzzetti et al.

[11] Patent Number: 5,965,563
[45] Date of Patent: Oct. 12, 1999

[54] ARYL AND HETEROARYL PURINE COMPOUNDS

[75] Inventors: Franco Buzzetti, Monza; Maria Gabriella Brasca, Cusago; Antonio Longo, Milan; Dario Ballinari, San Donato Milanese, all of Italy

[73] Assignee: Pharmacia & Upjohn S.p.A., Milan, Italy

[21] Appl. No.: 08/860,717

[22] PCT Filed: Oct. 14, 1996

[86] PCT No.: PCT/EP96/04460

§ 371 Date: Jul. 14, 1997

§ 102(e) Date: Jul. 14, 1997

[87] PCT Pub. No.: WO97/18212

PCT Pub. Date: May 22, 1997

[30] Foreign Application Priority Data

Nov. 14, 1995 [GB] United Kingdom ............... 9523242
Nov. 24, 1995 [GB] United Kingdom ............... 9524131

[51] Int. Cl.$^6$ .................. A61K 31/52; C07D 473/30; C07D 473/34; C07D 473/38
[52] U.S. Cl. .................. 514/261; 514/262; 514/266; 544/264; 544/265; 544/276; 544/277
[58] Field of Search ............... 544/264, 265, 544/276, 277; 514/261, 262, 266

[56] References Cited

U.S. PATENT DOCUMENTS

| | | | |
|---|---|---|---|
| 3,112,192 | 11/1963 | Feichtmeir et al. | 71/2.5 |
| 4,751,292 | 6/1988 | Fox | 536/24 |
| 4,853,386 | 8/1989 | Friebe et al. | 514/266 |

FOREIGN PATENT DOCUMENTS

| | | |
|---|---|---|
| 0181129 | 5/1986 | European Pat. Off. . |
| 0212535 | 3/1987 | European Pat. Off. . |
| 0414386 | 2/1991 | European Pat. Off. . |
| 828522 | 2/1960 | United Kingdom . |
| 90/09178 | 8/1990 | WIPO . |
| 9311106 | 6/1993 | WIPO . |
| 9606845 | 3/1996 | WIPO . |

OTHER PUBLICATIONS

Burke, "Protein–Tyrosine Kinases: Potential Targets for Anticancer Drug Development," Stem Cells, vol. 12, pp. 1–6, 1994.

*Primary Examiner*—Richard L. Raymond
*Assistant Examiner*—Ann M. Kessinger
*Attorney, Agent, or Firm*—Oblon, Spivak, McClelland, Maier & Neustadt, P.C.

[57] ABSTRACT

Novel bicyclic condensed pyrimidine compounds having general formula (I)

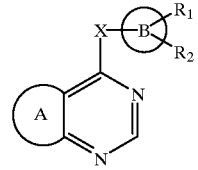

wherein X is —$CH_2$—, —NH—$(CH_2)_n$—, —O—$(CH_2)_n$— or —S—$(CH_2)_n$— in which n is zero or 1; A is a 4,5-fused imidazole ring N-substituted by $R_3$ which is hydrogen, $C_1$–$C_4$ alkyl or benzyl, or A is a 2,3-fused pyridine ring C-substituted by $R_4$ which is hydrogen, $C_1$–$C_4$ alkyl, $C_1$–$C_4$ alkoxy, halogen or $NR_5 R_6$ in which each of $R_5$ and $R_6$ independently is H or $C_1$–$C_4$ alkyl; B is a bicyclic ring chosen from tetralin, indane and 2-oxindole; each of $R_1$ and $R_2$ independently is hydrogen, $C_1$–$C_4$ alkyl, halogen, hydroxy, $C_1$–$C_4$ alkoxy, $C_1$–$C_4$ alkoxycarbonyl, nitro, cyano or $CF_3$; and the pharmaceutically acceptable salts thereof.

7 Claims, No Drawings

ARYL AND HETEROARYL PURINE COMPOUNDS

BACKGROUND OF THE INVENTION

1. Field of the Invention

The present invention relates to new bicyclic condensed pyrimidine compounds, to a process for their preparation, to pharmaceutical compositions containing them and to their use as therapeutic agents, in particular as tyrosine kinase inhibitors.

2. Description of the Background

EP-A-0414386 discloses 4-substituted pyrido[2,3-d] pyrimidine compounds which are plant fungicides, miticides and insecticides.

WO 90/09178 discloses 6,9-disubstituted purine compounds useful in adenosine-mediated lipolysis, cardiovascular diseases and broncodilatation.

SUMMARY OF THE INVENTION

The present invention provides novel bicyclic condensed pyrimidine compounds having the following general formula (I)

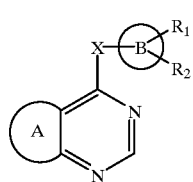

(I)

wherein

X is —$CH_2$—, —NH—$(CH_2)_n$—, —O—$(CH_2)_n$— or —S—$(CH_2)_n$— in which n is zero or 1;

A is a 4,5-fused imidazole ring N-substituted by $R_3$ which is hydrogen, $C_1$–$C_4$ alkyl or benzyl, or A is a 2,3-fused pyridine ring C-substituted by $R_4$ which is hydrogen, $C_1$–$C_4$ alkyl, $C_1$–$C_4$ alkoxy, halogen or $NR_5R_6$ in which each of $R_5$ and $R_6$ independently is H or $C_1$–$C_4$ alkyl;

B is a bicyclic ring chosen from tetralin, indane and 2-oxindole;

each of $R_1$ and $R_2$, independently, is hydrogen, $C_1$–$C_4$ alkyl, halogen, hydroxy, $C_1$–$C_4$ alkoxy, $C_1$–$C_4$ alkoxycarbonyl, nitro, cyano or $CF_3$;

and the pharmaceutically acceptable salts thereof; and wherein, when at the same time, A is pyridine and B is a tetralin ring, $R_4$ is H, $C_1$–$C_4$ alkyl, $C_1$–$C_4$ alkoxy or halogen and X is as defined above, then each of $R_1$ and $R_2$ is other than H; and wherein, when at the same time, A is imidazole, X is —NH—$(CH_2)_n$— as defined above, and B is an indan ring unsubstituted or substituted by one or more of halogen, hydroxy, $C_1$–$C_4$ alkoxy and nitro, then $R_3$ is other than $C_1$–$C_4$ alkyl or benzyl.

The X bridge may be located on either of the ring B moieties, preferably it is located on the benzene ring.

The $R_3$ substituent is only located on the imidazole ring on a N-ring atom.

The $R_4$ substituent is only located on the pyridine ring, preferably it is attached at the α-position.

The $R_1$ and $R_2$ substituents in tetralin and indan may be on either of the ring moieties, preferably they are attached to the benzene moiety. In 2-oxindole the $R_1$ and $R_2$ substituents are preferably located on the benzene moiety. Thus the $R_1$ and $R_2$ substituents are preferably attached to the benzene moiety when B is tetralin, indan or 2-oxindole.

The invention includes within its scope all the possible isomers, stereoisomers and their mixtures, and the metabolites and the metabolic precursors or bio-precursors (otherwise known as prodrugs) of the compounds of formula (I).

The X bridge is preferably linked to position 1 or 2 when B is tetralin and to position 5 when B is indane or 2-oxindole. Of course only one of the X, $R_1$ and $R_2$ substituents can be linked to the same position in ring B.

An alkyl group or an alkyl moiety in a alkoxy group may be branched or straight alkyl chains.

A $C_1$–$C_4$ alkyl group is preferably a $C_1$–$C_2$ alkyl, that is ethyl or methyl.

A $C_1$–$C_4$ alkoxy group is preferably a methoxy or ethoxy group.

A halogen atom is for example fluoro, chloro, bromo or iodio, in particular bromo or fluoro.

It is understood that when A is a 4,5-fused imidazole moiety then a purine ring is formed and when A is a 2,3-fused pyridine moiety then a pyrido[2,3-d]pyrimidine ring is formed.

The term tetralin is meant to refer to 5,6,7,8-tetrahydronaphthalene. In term X when X is —$NHCH_2$—, —$OCH_2$— or —$SCH_2$— it is understood that the linkage with the pyrimidine ring occurs through the N, 0 or S atom.

Pharmaceutically acceptable salts of the compounds of the invention include acid addition salts with inorganic acids, e.g. nitric, hydrochloric, hydrobromic, sulphuric, perchloric and phosphoric acid or organic acids, e.g. acetic, trifluoracetic, propionic, glycolic, lactic, oxalic, malonic, malic, maleic, tartaric, citric, benzoic, cinnamic, mandelic and salicylic acid.

As stated above, the present invention also includes within its scope pharmaceutically acceptable bio-precursors (otherwise known as prodrugs of the compounds of formula (I)), i.e. compounds which have different formula to formula (I) above but which, nevertheless, upon administration to a human being are converted directly or indirectly in vivo into a compound of formula (I).

Preferred compounds of the invention are the compounds of formula (I), wherein X, A and B are as defined above; $R_1$ is hydrogen or halogen, $R_4$ is hydrogen or $C_1$–$C_4$ alkoxy, and $R_2$ and $R_3$ are H; and the pharmaceutically acceptable salts thereof.

Examples of preferred specific compounds of formula (I) are the following compounds:

4-(2-oxindol-5-ylamino)-pyrido[2,3-d]pyrimidine;
7-methoxy-4-(2-oxindol-5-ylamino)-pyrido[2,3-d] pyrimidine;
4-(2-oxindol-5-ylmethylamino)-pyrido[2,3-d]pyrimidine;
7-methoxy-4-(2-oxindol-5-ylmethylamino)-pyrido[2,3-d] pyrimidine;
4-(2-oxindol-5-yloxy)-pyrido[2,3-d]pyrimidine;
7-methoxy-4-(2-oxindol-5-yloxy)-pyrido[2,3-d]pyrimidine;
4-(2-oxindol-5-ylmethoxy)-pyrido[2,3-d]pyrimidine;
7-methoxy-4-(2-oxindol-5-ylmethoxy)-pyrido[2,3-d] pyrimidine;
4-(2-oxindol-5-ylthio)-pyrido[2,3-d]pyrimidine;
7-methoxy-4-(2-oxindol-5-ylthio)-pyrido[2,3-d]pyrimidine;
4-(2-oxindol-5-ylmethylthio)-pyrido[2,3-d]pyrimidine;
7-methoxy-4-(2-oxindol-5-ylmethylthio)-pyrido[2,3-d] pyrimidine;
4-(2-oxindol-5-ylmethyl)-pyrido[2,3-d]pyrimidine;

7-methoxy-4-(2-oxindol-5-ylmethyl)-pyrido[2,3-d]pyrimidine;
4-(5-indanylamino)-pyrido[2,3-d]pyrimidine;
7-methoxy-4-(5-indanylamino)-pyrido[2,3-d]pyrimidine;
4-(5-indanylmethylamino)-pyrido[2,3-d]pyrimidine;
7-methoxy-4-(5-indanylmethylamino)-pyrido[2,3-d]pyrimidine;
4-(5-indanyloxy)-pyrido[2,3-d]pyrimidine;
7-methoxy-4-(5-indanyloxy)-pyrido[2,3-d]pyrimidine;
4-(5-indanylmethoxy)-pyrido[2,3-d]pyrimidine;
7-methoxy-4-(5-indanylmethoxy)-pyrido[2,3-d]pyrimidine;
4-(5-indanylthio)-pyrido[2,3-d]pyrimidine;
7-methoxy-4-(5-indanylthio)-pyrido[2,3-d]pyrimidine;
4-(5-indanylmethylthio)-pyrido[2,3-d]pyrimidine;
7-methoxy-4-(5-indanylmethylthio)-pyrido[2,3-d]pyrimidine;
4-(5-indanylmethyl)-pyrido[2,3-d]pyrimidine;
7-methoxy-4-(5-indanylmethyl)-pyrido[2,3-d]pyrimidine;
$N^6$-(1-tetralyl) adenine;
$N^6$-(3-bromo-1-tetralyl) adenine;
$N^6$-(5-indanyl) adenine;
$N^6$-(7-bromo-5-indanyl) adenine;
$N^6$-(2-oxindol-5-yl) adenine;
$N^6$-(1-tetralylmethyl) adenine;
$N^6$-(5-indanylmethyl) adenine;
$N^6$-(2-oxindol-5-ylmethyl) adenine;
6-(1-tetralyloxy)-purine;
6-(3-bromo-1-tetralyloxy)-purine;
6-(5-indanyloxy)-purine;
6-(7-bromo-5-indanyloxy)-purine;
6-(2-oxindol-5-yloxy)-purine;
6-(1-tetralylthio)-purine;
6-(3-bromo-1-tetralylthio)-purine;
6-(5-indanylthio)-purine;
6-(7-bromo-5-indanylthio)-purine;
6-(2-oxoindol-5-ylthio)-purine;
6-(1-tetralylmethyl)-purine;
6-(3-bromo-1-tetralylmethyl)-purine;
6-(5-indanylmethyl)-purine;
6-(7-bromo-5-indanylmethyl)-purine;
6-(2-oxindol-5-ylmethyl)-purine;
6-(1-tetralylmethoxy)-purine;
6-(5-indanylmethoxy)-purine;
6-(2-oxindol-5-ylmethoxy)-purine;
6-(1-tetralylmethylthio)-purine;
6-(5-indanylmethylthio)-purine; and
6-(2-oxindol-5-ylmethylthio)-purine;
either as single isomers or as a mixture thereof and the pharmaceutically acceptable salts thereof.

An object of the present invention is also to provide a bicyclic condensed pyrimidine compound of formula (I) as defined above, or a pharmaceutically acceptable salt thereof, for use as an active therapeutic substance, in particular as tyrosine kinase inhibitor.

A further object of the invention are pharmaceutical compositions comprising a compound of formula (I), as defined above, or a pharmaceutically salt thereof, as an active principle, and a pharmaceutically acceptable excipient (which can be a carrier and/or diluent).

A further object of the present invention is a bicyclic condensed pyrimidine compound of formula (IA)

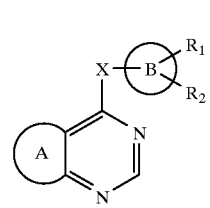

(IA)

wherein
X is $-CH_2-$, $-NH-(CH_2)_n-$, $-O-(CH_2)_n-$ or $-S-(CH_2)_n-$ in which
n is zero or 1;
A is a 2,3-fused pyridine ring C-substituted by $R_4$ which is hydrogen, $C_1-C_4$ alkyl, $C_1-C_4$ alkoxy, halogen or $NR_5R_6$ in which each of $R_5$ and $R_6$ independently is H or $C_1-C_4$ alkyl;
B is a bicyclic ring chosen from tetralin, indane and 2-oxindole;
each of $R_1$ and $R_2$, independently, is hydrogen, $C_1-C_4$ alkyl, halogen, hydroxy, $C_1-C_4$ alkoxy, $C_1-C_4$ alkoxycarbonyl, nitro, cyano or $CF_3$;
or a pharmaceutically acceptable salts thereof for use as an active therapeutic substance, in particular as tyrosine kinase inhibitor.

Examples of preferred specific compounds of formula (IA) are the following compounds:
4-(2-oxindol-5-ylamino)-pyrido[2,3-d]pyrimidine;
7-methoxy-4-(2-oxindol-5-ylamino)-pyrido[2,3-d]pyrimidine;
4-(2-oxindol-5-ylmethylamino)-pyrido[2,3-d]pyrimidine;
7-methoxy-4-(2-oxindol-5-ylmethylamino)-pyrido[2,3-d]pyrimidine;
4-(2-oxindol-5-yloxy)-pyrido[2,3-d]pyrimidine;
7-methoxy-4-(2-oxindol-5-yloxy)-pyrido[2,3-d]pyrimidine;
4-(2-oxindol-5-ylmethoxy)-pyrido[2,3-d]pyrimidine;
7-methoxy-4-(2-oxindol-5-ylmethoxy)-pyrido[2,3-d]pyrimidine;
4-(2-oxindol-5-ylthio)-pyrido[2,3-d]pyrimidine;
7-methoxy-4-(2-oxindol-5-ylthio)-pyrido[2,3-d]pyrimidine;
4-(2-oxindol-5-ylmethylthio)-pyrido[2,3-d]pyrimidine;
7-methoxy-4-(2-oxindol-5-ylmethylthio)-pyrido[2,3-d]pyrimidine;
4-(2-oxindol-5-ylmethyl)-pyrido[2,3-d]pyrimidine;
7-methoxy-4-(2-oxindol-5-ylmethyl)-pyrido[2,3-d]pyrimidine;
4-(5-indanylamino)-pyrido[2,3-d]pyrimidine;
7-methoxy-4-(5-indanylamino)-pyrido[2,3-d]pyrimidine;
4-(5-indanylmethylamino)-pyrido[2,3-d]pyrimidine;
7-methoxy-4-(5-indanylmethylamino)-pyrido[2,3-d]pyrimidine;
4-(5-indanyloxy)-pyrido[2,3-d]pyrimidine;
7-methoxy-4-(5-indanyloxy)-pyrido[2,3-d]pyrimidine;
4-(5-indanylmethoxy)-pyrido[2,3-d]pyrimidine;
7-methoxy-4-(5-indanylmethoxy)-pyrido[2,3-d]pyrimidine;
4-(5-indanylthio)-pyrido[2,3-d]pyrimidine;
7-methoxy-4-(5-indanylthio)-pyrido[2,3-d]pyrimidine;
4-(5-indanylmethylthio)-pyrido[2,3-d]pyrimidine;
7-methoxy-4-(5-indanylmethylthio)-pyrido[2,3-d]pyrimidine;
4-(5-indanylmethyl)-pyrido[2,3-d]pyrimidine;
7-methoxy-4-(5-indanylmethyl)-pyrido[2,3-d]pyrimidine;
4-(1-tetralylamino)-pyrido[2,3-d]pyrimidine;
7-methoxy-4-(1-tetralylamino)-pyrido[2,3-d]pyrimidine;
4-(1-tetralylmethylamino)-pyrido[2,3-d]pyrimidine;

7-methoxy-4-(1-tetralylmethylamino)-pyrido[2,3-d]
  pyrimidine;
4-(1-tetralyloxy)-pyrido[2,3-d]pyrimidine;
7-methoxy-4-(1-tetralyloxy)-pyrido[2,3-d]pyrimidine;
4-(1-tetralylmethoxy)-pyrido[2,3-d]pyrimidine;
7-methoxy-4-(1-tetralylmethoxy)-pyrido[2,3-d]pyrimidine;
4-(1-tetralylthio)-pyrido[2,3-d]pyrimidine;
7-methoxy-4-(1-tetralylthio)-pyrido[2,3-d]pyrimidine;
4-(1-tetralylmethylthio)-pyrido[2,3-d]pyrimidine;
7-methoxy-4-(1-tetralylmethylthio)-pyrido[2,3-d]
  pyrimidine;
4-(1-tetralylmethyl)-pyrido[2,3-d]pyrimidine; and
7-methoxy-4-(1-tetralylmethyl)-pyrido[2,3-d]pyrimidine;
either as single isomers or as a mixture thereof and the pharmaceutically acceptable salts thereof.

A further object of the invention are pharmaceutical compositions comprising a compound of formula (IA), as defined above, as an active principle and a pharmaceutically acceptable excipient (which can be a carrier and/or diluent).

The following compounds:
4-(1-tetralylamino)-pyrido[2,3-d]pyrimidine;
7-methoxy-4-(1-tetralylamino)-pyrido[2,3-d]pyrimidine;
4-(1-tetralylmethylamino)-pyrido[2,3-d]pyrimidine;
7-methoxy-4-(1-tetralylmethylamino)-pyrido[2,3-d]
  pyrimidine;
4-(1-tetralyloxy)-pyrido[2,3-d]pyrimidine;
7-methoxy-4-(1-tetralyloxy)-pyrido[2,3-d]pyrimidine;
4-(1-tetralylmethoxy)-pyrido[2,3-d]pyrimidine;
7-methoxy-4-(1-tetralylmethoxy)-pyrido[2,3-d]pyrimidine;
4-(1-tetralylthio)-pyrido[2,3-d]pyrimidine;
7-methoxy-4-(1-tetralylthio)-pyrido[2,3-d]pyrimidine;
4-(1-tetralylmethylthio)-pyrido[2,3-d]pyrimidine;
7-methoxy-4-(1-tetralylmethylthio)-pyrido[2,3-d]
  pyrimidine;
4-(1-tetralylmethyl)-pyrido[2,3-d]pyrimidine; and
7-methoxy-4-(1-tetralylmethyl)-pyrido[2,3-d]pyrimidine;
either as single isomers or as mixture thereof, which fall within the scope of formula (IA) and have been excluded from the scope of formula (I) by proviso, in view of the general disclosure provided by EP-A-0414386, have never been disclosed before as specific chemical entities.

Accordingly, such new compounds of formula (IA), either as single isomers or as a mixture thereof, and the pharmaceutically acceptable salts thereof are a further object of the present invention.

An object of the present invention is also to provide the use of a bicyclic condensed pyrimidine compound of formula (IB)

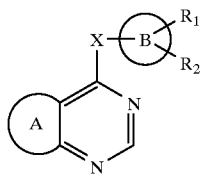

(IB)

wherein
  X is —CH$_2$—, —NH—(CH$_2$)$_n$—, —O—(CH$_2$)$_n$— or —S—(CH$_2$)$_n$— in which
  n is zero or 1;
  A is a 4,5-fused imidazole ring N-substituted by R$_3$ which is hydrogen, C$_1$–C$_4$ alkyl or benzyl, or A is a 2,3-fused pyridine ring C-substituted by R$_4$ which is hydrogen, C$_1$–C$_4$ alkyl, C$_1$–C$_4$ alkoxy, halogen or NR$_5$R$_6$ in which each of R$_5$ and R$_6$ independently is H or C$_1$–C$_4$ alkyl;
  B is a bicyclic ring chosen from tetralin, indane and 2-oxindole;
  each of R$_1$ and R$_2$, independently, is hydrogen, C$_1$–C$_4$ alkyl, halogen, hydroxy, C$_1$–C$_4$ alkoxy, C$_1$–C$_4$ alkoxycarbonyl, nitro, cyano or CF$_3$;
or a pharmaceutically acceptable salts thereof for use in the manufacture of a medicament having tyrosine kinase inhibiting activity.

Examples of preferred specific compounds of formula (IB) are the following compounds:
4-(2-oxindol-5-ylamino)-pyrido[2,3-d]pyrimidine;
7-methoxy-4-(2-oxindol-5-ylamino)-pyrido[2,3-d]
  pyrimidine;
4-(2-oxindol-5-ylmethylamino)-pyrido[2,3-d]pyrimidine;
7-methoxy-4-(2-oxindol-5-ylmethylamino)-pyrido[2,3-d]
  pyrimidine;
4-(2-oxindol-5-yloxy)-pyrido[2,3-d]pyrimidine;
7-methoxy-4-(2-oxindol-5-yloxy)-pyrido[2,3-d]pyrimidine;
4-(2-oxindol-5-ylmethoxy)-pyrido[2,3-d]pyrimidine;
7-methoxy-4-(2-oxindol -5-ylmethoxy)-pyrido[2,3-d]
  pyrimidine;
4-(2-oxindol-5-ylthio)-pyrido[2,3-d]pyrimidine;
7-methoxy-4-(2- oxindol-5-ylthio)-pyrido[2,3-d]
  pyrimidine;
4-(2-oxindol-5-ylmethylthio)-pyrido[2,3-d]pyrimidine;
7-methoxy-4-(2-oxindol-5-ylmethylthio)-pyrido[2,3-d]
  pyrimidine;
4-(2-oxindol-5-ylmethyl)-pyrido[2,3-d]pyrimidine;
7-methoxy-4-(2-oxindol-5-ylmethyl)-pyrido[2,3-d]
  pyrimidine;
4-(5-indanylamino)-pyrido[2,3-d]pyrimidine;
7-methoxy-4-(5-indanylamino)-pyrido[2,3-d]pyrimidine;
4-(5-indanylmethylamino)-pyrido[2,3-d]pyrimidine;
7-methoxy-4-(5-indanylmethylamino)-pyrido[2,3-d]
  pyrimidine;
4-(5-indanyloxy)-pyrido[2,3-d]pyrimidine;
7-methoxy-4-(5-indanyloxy)-pyrido[2,3-d]pyrimidine;
4-(5-indanylmethoxy)-pyrido[2,3-d]pyrimidine;
7-methoxy-4-(5-indanylmethoxy)-pyrido[2,3-d]pyrimidine;
4-(5-indanylthio)-pyrido[2,3-d]pyrimidine;
7-methoxy-4-(5-indanylthio)-pyrido[2,3-d]pyrimidine;
4-(5-indanylmethylthio)-pyrido[2,3-d]pyrimidine;
7-methoxy-4-(5-indanylmethylthio)-pyrido[2,3-d]
  pyrimidine;
4-(5-indanylmethyl)-pyrido[2,3-d]pyrimidine;
7-methoxy-4-(5-indanylmethyl)-pyrido[2,3-d]pyrimidine;
4-(1-tetralylamino)-pyrido[2,3-d]pyrimidine;
7-methoxy-4-(1-tetralylamino)-pyrido[2,3-d]pyrimidine;
4-(1-tetralylmethylamino)-pyrido[2,3-d]pyrimidine;
7-methoxy-4-(1-tetralylmethylamino)-pyrido[2,3-d]
  pyrimidine;
4-(1-tetralyloxy)-pyrido[2,3-d]pyrimidine;
7-methoxy-4-(1-tetralyloxy)-pyrido[2,3-d]pyrimidine;
4-(1-tetralylmethoxy)-pyrido[2,3-d]pyrimidine;
7-methoxy-4-(1-tetralylmethoxy)-pyrido[2,3-d]pyrimidine;
4-(1-tetralylthio)-pyrido[2,3-d]pyrimidine;
7-methoxy-4-(1-tetralylthio)-pyrido[2,3-d]pyrimidine;
4-(1-tetralylmethylthio)-pyrido[2,3-d]pyrimidine;
7-methoxy-4-(1-tetralylmethylthio)-pyrido[2,3-d]
  pyrimidine;
4-(1-tetralylmethyl)-pyrido[2,3-d]pyrimidine;
7-methoxy-4-(1-tetralylmethyl)-pyrido[2,3-d]pyrimidine;
N$^6$-(1-tetralyl) adenine;
N$^6$-(3-bromo-1-tetralyl) adenine;
N$^6$-(5-indanyl) adenine;
N$^6$-(7-bromo-5-indanyl) adenine;
N$^6$-(2-oxindol-5-yl) adenine;

N⁶-(1-tetralylmethyl) adenine;
N⁶-(5-indanylmethyl) adenine;
N⁶-(2-oxindol-5-ylmethyl) adenine;
6-(1-tetralyloxy)-purine;
6-(3-bromo-1-tetralyloxy)-purine;
6-(5-indanyloxy)-purine;
6-(7-bromo-5-indanyloxy)-purine;
6-(2-oxindol-5-yloxy)-purine;
6-(1-tetralylthio)-purine;
6-(3-bromo-1-tetralylthio)-purine;
6-(5-indanylthio)-purine;
6-(7-bromo-5-indanylthio)-purine;
6-(2-oxoindol-5-ylthio)-purine;
6-(1-tetralylmethyl)-purine;
6-(3-bromo-1-tetralylmethyl)-purine;
6-(5-indanylmethyl)-purine;
6-(7-bromo-5-indanylmethyl)-purine;
6-(2-oxindol-5-ylmethyl)-purine;
6-(1-tetralylmethoxy)-purine;
6-(5-indanylmethoxy)-purine;
6-(2-oxindol-5-ylmethoxy)-purine;
6-(1-tetralylmethylthio)-purine;
6-(5-indanylmethylthio)-purine; and
6-(2-oxindol-5-ylmethylthio)-purine;
either as single isomers or as a mixture thereof and the pharmaceutically acceptable salts thereof.

Object of the present invention is also to provide a pharmaceutical composition having tyrosine kinase inhibiting activity comprising a pharmaceutically acceptable carrier and/or diluent, and as an active principle a compound of formula (IB) or a pharmaceutically acceptable salt thereof.

The compounds of formula (I), (IA), (IB), and the pharmaceutically acceptable salts thereof, are altogether defined hereafter as the "compounds of the invention" or as the "active agents" of the invention.

The compounds of the invention can be obtained by an analogy process. In particular the compounds of formula (I), and the salts thereof, can be obtained by a process comprising:

a) reacting a compound of formula (II)

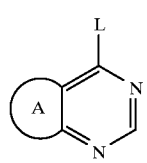
(II)

wherein A is as defined above and L is a leaving group with an amine compound of formula (III)

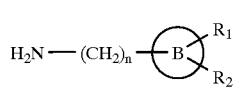
(III)

wherein n, B, $R_1$ and $R_2$ are as defined above, thus obtaining a compound of formula (I) in which X is —NH—$(CH_2)_n$—; or b) reacting a compound of formula (II) as defined above, with an hydroxy compound of formula (IV)

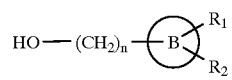
(IV)

wherein n, B, $R_1$ and $R_2$ are as defined above, thus obtaining a compound of formula (I) in which X is —O—$(CH_2)_n$—; or c) reacting a compound of formula (II) as defined above, with a thio compound of formula (V)

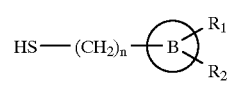
(V)

wherein n, B, $R_1$ and $R_2$ are as defined above, thus giving a compound of formula (I) in which X is —S—$(CH_2)_n$—; or d) reacting a compound of formula (VI)

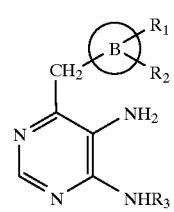
(VI)

wherein B, $R_1$, $R_2$ and $R_3$ are as defined above, with formamide ($HCONH_2$), thus providing a compound of formula (I) wherein X is —$CH_2$— and A is a 4,5-fused imidazole ring; or e) hydrolyzing and decarboxylating a compound of formula (VII)

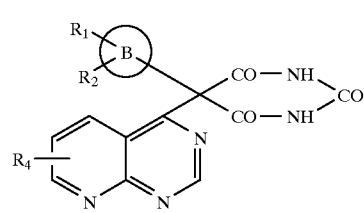
(VII)

wherein B, $R_1$, $R_2$ and $R_4$ are as defined above, thus providing a compound of formula(I), wherein X is —$CH_2$— and A is a 2,3-fused pyridine ring;

and, if desired, converting a compound of formula (I) into another compound of formula (I), and/or, if desired, converting a compound of formula (I) into a salt thereof, and/or, if desired, converting a salt of a compound of formula (I) into a free compound of formula (I), and/or, if desired, separating a mixture of isomers of a compound of formula (I) into the single isomers.

A leaving group L in a compound of formula (II) is for instance chloro, 1,2,4-triazol-1-yl or methylthio.

The reaction of a compound of formula (II) with a compound of formula (III) according to process step a) may be carried out using known methods, e.g. as described by Bullock et al. in J.Am.Chem.Soc. 78, 3693 (1956). The reaction is carried out in the presence of a suitable organic inert solvent, for example an alkanol or ester such as methanol, ethanol, isopropanol, methyl cellosolve or ethyl acetate, a halogenated solvent such as dichloromethane or chloroform, an ether such as tetrahydrofuran or dioxane, a dipolar aprotic solvent such as dimethylformamide or dimethylacetamide. Preferably the solvents isopropanol or methyl cellosolve are used. The reaction is conveniently carried out at a temperature in the range from about 10 to about 150° C., preferably in the range from about 20 to about 80° C. In general only 1 equivalent of amine compound (III) is used, thus giving the hydrochloride salt, which precipitates on cooling. To obtain the free base from the salt, the salt may be treated with a suitable base in the presence of an appropriate solvent such as the ones mentioned above. Suitable bases are e.g. organic amines such as triethylamine or pyridine, or inorganic bases such as sodium carbonate or sodium hydroxide. Alternatively to obtain directly the free base of formula (I) one may apply more than 2 equivalent of amine compound (III) in the reaction.

The reaction of a compound of formula (II) with a compound of formula (IV) according to process step b) may be carried out by using known methods, e.g. as described by Prasad et al. in J.Am.Chem.Soc. 79, 6401 (1957). The reaction is preferably carried out in a protic solvent, e.g. water or aqueous alkanol such as aqueous methanol, ethanol or isopropanol in the presence of a suitable alkali base such as sodium or potassium hydroxide. The reaction temperatures are ranging from about 0 to about 100° C., preferably the range is from about 50 to about 100° C. Alternatively the hydroxy compound of formula (IV) is at first transformed into its metal salt in an aprotic solvent, which is then reacted with the compound of formula (II). For example the metallation of compound (IV) may be carried out with metal compounds like NaH or NaNH$_2$ in an aprotic solvent such as tetrahydrofuran, ethyl ether, DMF or benzene. The metal salt is then reacted with compound (II) in the same aprotic solvent at temperatures ranging from about 0 to about 100° C., preferably in the range from about 20 to about 40° C.

The reaction of a compound of formula (II) with a thiol compound of formula (V) according to process step c) may be carried out using known methods, e.g. as reviewed in Heterocyclic Compounds vol.8, page 335 (1967, Editor R. C. Elderfield). Suitable reaction solvents are protic solvents, e.g. water, alkanols such as methanol, ethanol and isopropanol or ethers such as tetrahydrofuran or dioxane. In order to obtain the corresponding metal mercaptide, which is the actual reactant, the reaction is carried out in the presence of a suitable alkali base, e.g. an alkali hydroxide such as sodium or potassium hydroxide, an alkali alkoxide such as sodium or potassium methoxide, sodium or potassium ethoxide or sodium or potassium methoxyethoxide. The reaction temperature may vary from about 0 to about 120° C., preferably from about 40 to about 80° C.

The cyclization of the ortho diamino compound of formula (VI) according to process step d) may be carried out by known methods, e.g. as reviewed in Rodd's Chemistry of Carbon Compounds vol.IV, part L, page 5 (1980, Elsevier Scientific Publishing Company). Hereto an important modification of the Traube cyclization method can be applied which uses formamide instead of formic acid, e.g. as described by Daly et al. in J.Org.Chem. 21, 177 (1956). Accordingly the compound (VI) is cyclized in formamide solution at temperatures ranging from about 100 to about 210° C., preferably at reflux temperature.

The hydrolysis and decarboxylation of a compound of formula (VII) according to process step e) may be carried out using known methods, e.g. as described in J.Het.Chem. 14, 1081 (1977) by A.Scoville and F. X. Smith. Suitable reaction solvents are protic solvents, e.g. water or aqueous alkanols such as methanol, ethanol or isopropanol. The hydrolysis step is carried out in alkaline conditions, e.g. in the presence of an alkali hydroxide such as sodium or potassium hydroxide. The reaction temperature may range from room to reflux temperature, preferably reflux temperature is applied. The decarboxylation step is carried out in slightly acidic conditions, e.g. in the presence of a mineral acid such as hydrochloric acid. The reaction temperature may vary from room to reflux temperature, preferably reflux temperature is used.

The optional salification of a compound of formula (I) as well as the conversion of the salt into the corresponding free compound and the separation of the mixture of isomers into the single isomers as well as the conversion of a compound of formula (I) into another compound of formula (I) may be carried according to known methods.

The conversion of a compound of formula (I), wherein A is a 4,5-fused imidazole ring and R$_3$ is H, into the respective compound of formula (I), wherein R$_3$ is C$_1$–C$_4$ alkyl or benzyl, may be carried out by known N-alkylation methods, e.g. as mentioned in Heterocyclic Compounds vol.8, page 378 (1967, editor R. C. Elderfield). Accordingly a C$_1$–C$_4$ alkyl or benzyl halide is reacted with the N$^9$-unsubstituted purine in an appropriate organic solvent, preferably in a dipolar aprotic solvent such as DMF, DMAA or DMSO, and in the presence of an inorganic base such as sodium hydroxide or potassium carbonate.

The conversion of a compound of formula (I), wherein X is —O—(CH$_2$)$_n$— or —S—(CH$_2$)$_n$— into a compound (I), wherein X is —NH—(CH$_2$)$_n$— can be carried out, according known methods, by a displacement reaction with an amine compound of formula (III) as defined above. E.g. according to Elion et al. in J.Am.Chem.Soc. 74, 411 (1952) the thio compound of formula (I) is heated with the amine compound of formula (III) in aqueous solution in a sealed tube at temperatures ranging from about 130 to about 180° C.

The compounds of formula (II), wherein A is a 4,5-fused imidazole ring and L is chloro, are known or may be obtained from a compound of formula (VIII)

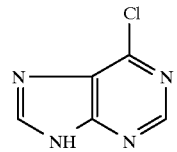

(VIII)

by known N-alkylation methods, e.g. as reviewed in Heterocyclic Compounds vol.8, page 372 (1967, Editor R. C. Elderfield) and as mentioned above.

The compound of formula (VIII) is commercially available.

The compounds of formula (II), wherein A is a 2,3-fused pyridine ring, are known or may be obtained by known methods from known compounds. For example the 4-chloro compounds of formula (II), wherein A is a 2,3-fused pyridine ring and L is chloro are prepared by chlorodehydroxylation of the corresponding 4-hydroxy-pyrido[2,3-d]pyrimidine derivatives of formula (IX)

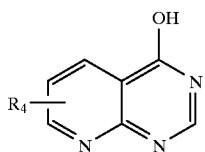

using conventional methods, e.g. by reaction with $POCl_3$. The intermediate of formula (II), wherein A is a 2,3-fused pyridine ring and L is 1,2,4-triazol-1-yl, can be prepared e.g. by adding gradually $POCl_3$ to a mixture of compound of formula (IX) (1 equivalent) and 1,2,4-triazole (3 equivalent) in pyridine solution at temperatures ranging from room to reflux temperatures.

The compounds of formula (IX) are known or may be obtained by known methods from known compounds. For example 4-hydroxy-pyrido[2,3-d]pyrimidine is obtained from 2-aminonicotinic acid by condensation with formamide as described in J.Am.Chem.Soc. 77, 2256 (1955) by R. K. Robins and G. H. Hitchings.

The compounds of formula (VII) can be made by using the process of A.Scoville and F. X. Smith as described in J.Het.Chem. 14, 1081 (1977). Accordingly a compound of formula (II), in which L is chloro, A is a 2,3-fused pyridine ring and $R_4$ is as defined above, is reacted with a compound of formula (X)

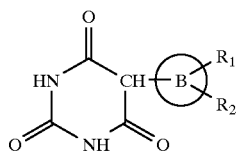

in which B, $R_1$ and $R_2$ are as defined above.

The compounds of formulae (III), (IV), (V), (VI), and (X) are either known compounds or may be obtained by known methods from known compounds.

When in the new compounds of the present invention and in the intermediate products used for their preparation there are groups present which need to be protected before the above-described reactions are performed, they may be protected before the reaction takes place and then deprotected at the end of the reaction, according to well known methods in organic chemistry.

The new compounds of formula (IA) can be analogously obtained.

PHARMACOLOGY

The compounds of the invention possess specific tyrosine kinase inhibiting activity. It is believed that tyrosine kinase inhibitors may be of great importance in the control of uncontrolled cellular reproduction, i.e. in cellular reproduction disorders. Hence, the compounds according to the present invention can be useful in the treatment of pathological proliferation disorders in mammals, including humans. Typical examples of such disorders are tumors, including leukemia, and psoriasis. The compounds of the invention can also be useful in inhibiting the development of the atheromatous plaque and in the control of angiogenesis and as anti-metastatic agents.

Recent studies on the molecular basis of the neoplastic transformation have identified a family of genes, designed oncogenes, whose aberrant expression causes tumorigenesis. For example, the RNA tumor viruses possess such an oncogene sequence whose expression determines neoplastic conversion of infected cells. Several of their oncogene-encoded proteins, such as $pp60^{v\text{-}src}$, $p70^{gag\text{-}yes}$, $p13^{gag\text{-}fPs}$ and $p70^{gag\text{-}fgr}$ display protein tyrosine kinase activity, that is they catalyze the transfer of the g-phosphate from adenosine triphosphate (ATP) to tyrosine residues in protein substrate. In normal cells, several growth factor receptors, for example the receptors for PDGF, EGF, α-TGF and insulin, display tyrosine kinase activity. Binding of the growth factor (GF) activates the receptor tyrosine kinase to undergo autophosphorylation and to phosphorylate closely adjacent molecules on tyrosine. Therefore, it is thought that the phosphorylation of these tyrosine kinase receptors plays an important role in signal transduction and the principal function of tyrosine kinase activity in normal cells is to regulate cell growth. Perturbation of this activity by oncogenic tyrosine kinases that are either overproduced and/or display altered substrate specificity may cause loss of growth control and/or neoplastic transformation. Accordingly, a specific inhibitor of tyrosine kinase can be useful in investigating the mechanism of cancerogenesis, cell proliferation and differentiation and it can be effective in the prevention and chemotherapy of cancer and in other pathological proliferative conditions.

Hence the compounds according to the present invention can be useful in the treatment of pathological proliferation disorders in mammals, including humans.

A human or animal, e.g. a mammal, can thus be treated by a method comprising the administration thereto of a therapeutically effective amount of one of the compounds of the invention. In this way the condition of the human or animal may be improved. Amelioration of the disease state or disorder from which the human or animal is suffering can be achieved. Typical examples of such disorders are benign and malignant tumours, including leukemia such as myeloblastic leukaemia, lymphoma, sarcoma, neuroblastoma, Wilm's tumour, malignant neoplasm of the bladder, breast, lung or thyroid, neoplasias of epithelial origin, such as mammacarcinoma. Moreover, they can be useful in the treatment of epidermal hyperproliferation, such as psoriasis. The compounds of the invention can also be useful in inhibiting the development of the atheromatous plaque and restenosis, in the control of angiogenesis, as anti-metastatic agents and in treating diabetic complications. They have also utility in the control of immune system diseases, e.g. as immunosuppressants, as far as protein tyrosine kinases, particularly Zap70, p56 lck and p59 fyn, are strongly involved in the control of the proliferation of the immune system. Moreover, the compounds of the invention have utility in the treatment of Alzheimer's disease due to the pivotal role played by tyrosine phosphorylation (e.g. Tau proteins) in the development of the disease.

The tyrosine specific protein kinase activity of the compounds of the invention is shown, e.g., by the fact that they are active in the in vitro and in vivo test described herebelow.

EGFR-Autophosphorylation Assay (AMIKA assay)

The EGFR autophosphorylation was assayed using A431 crude membrane extracts as source of the receptor.
Membrane purification Membranes were prepared as reported by A. Levitzky et al. (Methods in Enzymology 201, 347 (1991) with minor modifications and adapting the method to the A431 human epidermoid carcinoma cell line. Briefly, low density cells growing in RPMI 1640 plus 10% foetal calf serum were detached using 1 mM EDTA in phosphate buffer saline (PBS) and lysed in cold Lysing buffer (1 ml/10$^6$cells) (20 mM HEPES pH 7.6, 10 mM NaCl, 2 mM EDTA, 10 µg/ml Aprotinin, 10 µg/ml Luepeptin, 1 mM PMSF). Cells were homogenized by 10 strokes in Dounce homogenizer. Nuclei and debris were removed by low speed centrifugation. Membranes were pelletized by ultracentrifugation (1 h, 100000×g) and resuspended in cold HNG buffer (50 mM HEPES pH 7.6, 125 mM NaCl, 10% glycerol) Protein concentration, determined by Pierce BCA method, was adjusted to 1.5–2 mg/ml. Aliquots were stored at −80° C.

Determination of IC$_{50}$

To determine the IC$_{50}$ A431 membranes (2.5 mg of protein/sample) pre-treated with EGF (final concentration 200 nM) for 30 min at 4° C. were incubated in 30 µl of reaction buffer (50 mM HEPES pH 7.6, 125 mM NaCl, 12 mM Mg-acetate, 2 mM MnCl$_2$, 1 mM NaVO$_3$, 1 mM ATP, 1 mCi γ-$^{32}$P-ATP) for 1 min at 0° C. in the presence of increasing concentrations of compounds. The reaction was stopped with Laemly solution. The samples were heated 5 min at 95° C. and submitted to SDS-PAGE (7.5% acrylamide gel). Gels were fixed in 40% methanol:10% acetic acid for 1 h and washed overnight with 20% methanol:7% acetic acid. After 15 min in 50% methanol:2% glycerol gels were dried and exposed overnight. Bands corresponding to EGFR were excised from the gels and counted in a β-counter.

Inhibition of cellular tyrosine autophosphorylation (VAP assay)

EGF is able to induce the phosphorylation in tyrosine of a specific set of intracellular proteins including EGFR itself. This increase in tyrosine phosphorylation was measured using the Vectastain-ABC-AP kit (Vector Laboratories) following the manufacturer's instructions. Briefly, 2×10$^4$ A431 cells per well were plated into a microtiter plate and incubated for 3 days at 37° C./ 5% CO$_2$ until the cultures reached confluency.

Cell monolayers were washed with PBS and covered with fresh medium containing 0.1% bovine serum albumin (BSA). Serial dilution of test compounds were added 2 h before the addition of 100 ng/ml EGF; after 10 min stimulation the culture medium was withdrawn, cells were washed 2 times with PBS and fixed for 10 min with cold methanol (−20° C.). After fixation 200 ml of blocking solution (3% BSA in PBS, 0.2% Tween 20, 1% normal horse serum) were added for 1 h at 37° C. Blocking solution was replaced with 3% BSA in PBS containing the antiphosphotyrosine antibody 4G10 (UBI) diluted 1:30000 and incubated for 1 h. Bound antibodies were revealed using the Vectastain-ABC-AP kit with p-nitrophenyl phosphate as the substrate. Reaction was developed for 30 min in the dark and the plates were read at 405 nm.

SRB-Antiproliferative assay (A431 assay)

The antiproliferative activity of the test compounds was assayed on A431 cells using the SRB calorimetric method (P. Skehan et al.: J.Natl.Cancer Inst.1990, 82, 1107–1112). A431 cells were seeded into 96-well microtiter plates (5000 cells/cm$^2$) and incubated overnight at 37° C./5% CO$_2$. Compounds dissolved in DMSO were added in serial dilution and plates were incubated for 3 days at 37° C./5% CO$_2$. Cells were fixed with cold TCA (10% final concentration) and stained with 0.4% Sulforhodamine B dye in 1% acetic acid for 30 min. Dye was solubilized with 10 mM Tris (pH 10.4) and microtiters were read at 550 nm.

In view of their high activity, the compounds of the invention can be used safely in medicine.

The compounds of the invention can be administered in a variety of dosage forms, e.g. orally, in the forms of tablets, capsules, sugar- and film-coated tablets, liquid solutions or suspensions; rectally, in the form of suppositories; parenterally, e.g. intramuscularly, or by intravenous injection or infusion; or topically. The dosage depends on the age, weight, condition of the patient and administration route. For example, the dosage adopted for oral administration to adult humans for the compounds 4-(5-indanylamino)-pirido [2,3-d]pyrimidine and N$^6$-(1-tetralyl)-adenine may range from about 5 to about 150–200 mg per dose, from 1 to 5 times daily. Of course, these dosage regimes may be adjusted to provide the optimal therapeutic response.

The pharmaceutical compositions containing the compounds of the invention are usually prepared following conventional methods and are administered in a pharmaceutically suitable form.

For example, the solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate, effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, by means of mixing, granulating, tabletting, sugar-coating or film-coating processes.

The liquid dispersion for oral administration may be, e.g., syrups, emulsions and suspensions.

The syrup may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride.

The solutions for intravenous injections or infusions may contain as carrier, for example, sterile water or, preferably, they may be in the form of sterile aqueous, isotonic saline solutions.

The suppositories may contain, together with the active compound, a pharmaceutically acceptable carrier, e.g. cocoabutter, polyethylene glycol, a polyoxyethylene sorbitan fatty acid ester surfactant or lecithin.

Compositions for topical application, e.g. creams, lotions or pastes, can be prepared by admixing the active ingredient with a conventional oleaginous or emulsifying excipient.

A further object of the present invention is a combined method of treatment of cancer or of amelioration of the conditions of mammals, including humans, suffering from cancer, said method comprising administering 1) a compound of the invention, that is a compound of formula (I), (IA) or (IB) or a pharmaceutically acceptable salt thereof, and 2) an additional antitumor agent, in amounts and close enough together in time sufficient to produce a therapeutically useful effect.

The present invention also provides products containing a compound of the invention, that is a compound of formula (I), (IA) or (IB) or a pharmaceutically acceptable salt thereof, and an additional antitumor agent as a combined preparation for simultaneous, separate or sequential use in anticancer therapy.

The term "antitumour agent" is meant to comprise both a single antitumour drug and "cocktails", i.e. a mixture of such drugs, according to the clinical practice.

Examples of antitumour agents that can be formulated with a compound of the invention or, alternatively, can be administered in a combined method of treatment, include doxorubicin, daunomycin, epirubicin, idarubicin, etoposide, fluorouracil, melphalan, cyclophosphamide, bleomycin, vinblastin and mitomycin or a mixture of two or more thereof.

The compounds of the invention can therefore be used in a treatment to ameliorate a cancer. They may be administered to a patient suffering from a cancer treatable with an antitumour agent, for example an anthracycline glycoside such as doxorubicin, daunomycin, epirubicin or idarubicin as mentioned above, together with the antitumour agent.

A compound of the invention and an antitumour agent such as an anthracycline glycoside can be administered to improve the condition of a patient having leukemia such as myeloblastic leukemia, lymphoma, sarcoma, neuroblastoma, Wilm's tumour or malignant neoplasm of the bladder, breast, lung or thyroid.

Accordingly, the present invention provides a method of treating a patient in need of a tyrosine kinase inhibitor, the method comprising administering to said patient a therapeutically effective amount of a compound of formula (I), (IA) or of formula (IIB), as defined above, or a pharmaceutically acceptable salt thereof.

The following examples illustrate but do not limit the invention.

EXAMPLE 1

4-(5-indanylamino)-pyrido[2,3-d]pyrimidine hydrochloride

A solution of 6-chloropyrido[2,3-d]pyrimidine (1.656 g, 10 mM) and 5-aminoindan (1.332 g, 10 mM) in isopropanol (60 ml) is heated to reflux for about 20 h. The resulting salt suspension is then cooled to room temperature, filtered and the residue washed with ice-cooled isopropanol to give almost pure title compound in about 80% yield.

| $C_{16}H_{15}ClN_4$ | calcd: | C 64.32 | H 5.06 | Cl 11.86 | N 18.75 |
|---|---|---|---|---|---|
| | found: | C 64.05 | H 4.96 | Cl 11.65 | N 18.55 |

MS m/z 298

According to the above described procedure the following compounds can be prepared:
7-methoxy-4-(5-indanylamino)-pyrido[2,3-d]pyrimidine hydrochloride;
4-(5-indanylmethylamino)-pyrido[2,3-d]pyrimidine hydrochloride
7-methoxy-4-(5-indanylmethylamino)-pyrido[2,3-d] pyrimidine hydrochloride;
4-(2-oxindol-5-ylamino)-pyrido[2,3-d]pyrimidine hydrochloride;
7-methoxy-4-(2-oxindol-5-ylamino)-pyrido[2,3-d] pyrimidine hydrochloride;
4-(2-oxindol-5-ylmethylamino)-pyrido[2,3-d]pyrimidine hydrochloride;
7-methoxy-4-(2-oxindol-5-ylmethylamino)-pyrido[2,3-d] pyrimidine hydrochloride;
4-(1-tetralylamino)-pyrido[2,3-d]pyrimidine hydrochloride;
7-methoxy-4-(1-tetralylamino)-pyrido[2,3-d]pyrimidine hydrochloride;
4-(1-tetralylmethylamino)-pyrido[2,3-d]pyrimidine hydrochloride; and
7-methoxy-4-(1-tetralylmethylamino)-pyrido[2,3-d] pyrimidine hydrochloride.

EXAMPLE 2

4-(5-indanylamino)-pyrido[2,3-d]pyrimidine

A suspension of 4-(5-indanylamino)-pyrido[2,3-d] pyrimidine hydrochloride (2.988 g, 10 mM) and potassium carbonate (2.764 g, 20 mM) in methanol (60 ml) is stirred at ambient temperature for 0.5 h. The mixture is filtered and the filtrate evaporated under vacuum. The residue is purified by column chromatography using a 93:7 mixture of dichloromethane/methanol as eluant to give pure title compound in 90% yield.

| $C_{16}H_{14}N_4$ | calcd: | C 73.26 | H 5.38 | N 21.36 |
|---|---|---|---|---|
| | found: | C 73.15 | H 5.25 | N 21.15 |

MS m/z 262

By proceeding analogously the following compounds can be prepared:
7-methoxy-4-(5-indanylamino)-pyrido[2,3-d]pyrimidine;
4-(5-indanylmethylamino)-pyrido[2,3-d]pyrimidine;
7-methoxy-4-(5-indanylmethylamino)-pyrido[2,3-d] pyrimidine;
4-(2-oxindol-5-ylamino)-pyrido[2,3-d]pyrimidine;
7-methoxy-4-(2-oxindol-5-ylamino)-pyrido[2,3-d] pyrimidine;
4-(2-oxindol-5-ylmethylamino)-pyrido[2,3-d]pyrimidine;
7-methoxy-4-(2-oxindol-5-ylmethylamino)-pyrido[2,3-d] pyrimidine
4-(1-tetralylamino)-pyrido[2,3-d]pyrimidine;
7-methoxy-4-(1-tetralylamino)-pyrido[2,3-d]pyrimidine;
4-(1-tetralylmethylamino)-pyrido(2,3-d]pyrimidine; and
7-methoxy-4-(1-tetralylmethylamino)-pyrido[2,3-d] pyrimidine.

EXAMPLE 3

4-(5-indanyloxy)-pyrido[2,3-d]pyrimidine

To a solution of 5-hydroxyindan (1.342 g, 10 mM) in 80 ml of aqueous potassium hydroxide solution containing 1.683 g (30 mM) of solid potassium hydroxide is added 6-chloro-pyrido[2,3-d] pyrimidine (1.656 g, 10 mM). The reaction mixture is stirred for about 0.5 h at room temperature until most of the 6-chloro-pyrido[2,3-d]pyrimidine dissolves and then heated on the steam bath for further 0.5 h. The mixture is cooled, filtered and the residue recrystallized from hot aqueous ethanol to give pure title compound in 60% yield.

| $C_{16}H_{13}N_3O$ | calcd: | C 72.99 | H 4.97 | N 15.96 |
|---|---|---|---|---|
| | found: | C 72.65 | H 4.91 | N 15.85 |

MS m/z 263

According to the above described procedure the following compounds can be prepared:
4-(2-oxindol-5-yloxy)-pyrido[2,3-d]pyrimidine;
7-methoxy-4-(2-oxindol-5-yloxy)-pyrido[2,3-d]pyrimidine;
4-(2-oxindol-5-ylmethoxy)-pyrido[2,3-d]pyrimidine;

7-methoxy-4-(2-oxindol-5-ylmethoxy)-pyrido[2,3-d] pyrimidine;
7-methoxy-4-(5-indanyloxy)-pyrido[2,3-d]pyrimidine;
4-(5-indanylmethoxy)-pyrido[2,3-d]pyrimidine;
7-methoxy-4-(5-indanylmethoxy)-pyrido[2,3-d]pyrimidine;
4-(1-tetralyloxy)-pyrido[2,3-d]pyrimidine;
7-methoxy-4-(1-tetralyloxy)-pyrido[2,3-d]pyrimidine;
4-(1-tetralylmethyloxy)-pyrido[2,3-d]pyrimidine; and
7-methoxy-4-(1-tetralylmethyloxy)-pyrido[2,3-d] pyrimidine.

EXAMPLE 4

4-(5-indanylthio)-pyrido[2,3-d]pyrimidine

To a solution of 6-chloropyrido[2,3-d]pyrimidine (1.656 g, 10 mM) in methanol (30 ml) is added a solution of 1-mercaptoindan (4.506 g, 30 mM) in methanolic potassium hydroxide (60 ml containing 1.608 g (30 mM) solid potassium hydroxide). The reaction mixture is stirred for 0.5 h at room temperature and then boiled for 0.5 h at reflux. The solution is concentrated under vacuum and then cooled to give crystalline title compound in about 60% yield.

| $C_{16}H_{13}N_3S$ | calcd: | C 68.79 | H 4.69 | N 15.04 | S 11.48 |
|---|---|---|---|---|---|
| | found: | C 68.65 | H 4.55 | N 14.75 | S 11.30 |

MS m/z 279

By proceeding analogously the following compounds can be prepared:
4-(2-oxindol-5-ylthio)-pyrido[2,3-d]pyrimidine;
7-methoxy-4-(2-oxindol-5-ylthio)-pyrido[2,3-d]pyrimidine;
4-(2-oxindol-5-ylmethylthio)-pyrido[2,3-d]pyrimidine;
7-methoxy-4-(2-oxindol-5-ylmethylthio)-pyrido[2,3-d] pyrimidine;
7-methoxy-4-(5-indanylthio)-pyrido[2,3-d]pyrimidine;
4-(5-indanylmethylthio)-pyrido[2,3-d]pyrimidine;
7-methoxy-4-(5-indanylmethylthio)-pyrido[2,3-d] pyrimidine;
4-(1-tetralylthio)-pyrido[2,3-d]pyrimidine;
7-methoxy-4-(1-tetralylthio)-pyrido[2,3-d]pyrimidine;
4-(1-tetralylmethylthio)-pyrido[2,3-d]pyrimidine; and
7-methoxy-4-(1-tetralylmethylthio)-pyrido[2,3-d] pyrimidine.

EXAMPLE 5

4-(5-indanylmethyl)-pyrido[2,3-d]pyrimidine

A solution of 5-(5-indanyl)-5-(pyrido[2,3-d]pyrimidin-4-yl) barbituric acid (3.734 g, 10 mM) and sodium hydroxide (2.00 g, 50 mM) in water (40 ml) is refluxed for 15 h. After cooling the solution is made slightly acidic (pH4–5) by addition of HCl and again refluxed for 15 h. The solution is cooled, made strongly basic with sodium hydroxide and then extracted with ethyl acetate. The organic phase is washed with water, dried and then evaporated to dryness under vacuum. The residue is purified by column chromatography using dichloromethane/methanol 93:7 as eluant. Thus pure title compound is obtained in about 60% yield.

By proceeding analogously the following compounds can be prepared:
4-(2-oxindol-5-ylmethyl)-pyrido[2,3-d]pyrimidine;
7-methoxy-4-(2-oxindol-5-ylmethyl)-pyrido[2,3-d] pyrimidine;
7-methoxy-4-(5-indanylmethyl)-pyrido[2,3-d]pyrimidine;
4-(1-tetralylmethyl)-pyrido[2,3-d]pyrimidine; and
7-methoxy-4-(1-tetralylmethyl)-pyrido[2,3-d]pyrimidine.

EXAMPLE 6

4-(5-indanylamino)-pyrido[2,3-d]pyrimidine

A suspension of 4-(5-indanylthio)-pyrido[2,3-d] pyrimidine (2.79 g, 10 mM) and 5-aminoindan (3.996 g, 30 mM) in water (100 ml) is heated in a sealed tube at 130° C. for 20 h. Then the water is evaporated under vacuum and the residue chromatographed on silica gel by using dichloromethane/methanol mixtures as eluant. Thus almost pure title compound is obtained in about 40% yield.

| $C_{16}H_{14}H_4$ | calcd: | C 73.26 | H 5.38 | N 21.36 |
|---|---|---|---|---|
| | found: | C 73.01 | H 5.15 | N 21.05 |

MS m/z 262

EXAMPLE 7

5-(5-indanyl)-5-(pyrido[2,3-d]pyrimidin-4-yl) barbituric acid

A slurry of 4-chloro-pyrido[2,3-d]pyrimidine (1.656 g, 10 mM) and 5-(5-indanyl) barbituric acid (2.443 g, 10 mM) is stirred in an oil bath. The temperature is raised to 130° C. in a period of 15 min. Then the temperature is further increased from 130° C. to 170° C. During this period apparently a reaction occurs since the slurry solidifies. The resulting solid is maintained for further 10 min at about 170° C. Then the reaction mixture is cooled, triturated with sodium bicarbonate solution and hexane. The solid is filtered off, washed with water and dried under vacuum. The raw product is submitted to the next step without further purification.

EXAMPLE 8

4-chloro-pyrido[2,3-d]pyrimidine

A mixture of pyrido[2,3-d]pyrimidin-4(3H)-one (1.471 g, 10 mM) and POCl$_3$ (16 ml) is stirred for 1 h at reflux. The excess of POCl$_3$ is removed under vacuum. Then dichloromethane and iced water is added and the mixture stirred until the black solid dissolves. The organic layer is separated, washed with bicarbonate solution, dried over Na$_2$SO$_4$ and then evaporated to dryness. The yellow residue is recrystallized from toluene/hexane to give almost pure title compound in 70% yield. mp 137° C.

EXAMPLE 9

Pyrido[2,3-d]pyrimidin-4(3H)-one 2-aminonicotinic acid (1.381 g, 10 mM) and formamide (2.70 g, 60 mM) are heated at 165–170° C. for 2 h by means of an oil bath. The reaction mixture is cooled and the resulting solid recrystallized from water to give about 1.030 g of title compound (70% yield). mp 255–8° C.

EXAMPLE 10

N$^6$-(1-tetralyl) adenine hydrochloride salt

A solution of 6-chloropurine (1.546 g, 10 mM) and 1-aminotetralin(1.472 g, 10 mM) in isopropanol (60 ml) is heated to reflux for about 20 h. The resulting salt suspension is then cooled to room temperature, filtered and the residue washed with ice-cooled isopropanol to give almost pure title compound in 80% yield.

| $C_{15}H_{16}ClN_5$ | calcd: | C 59.70 | H 5.34 | Cl 11.75 | N 23.21 |
|---|---|---|---|---|---|
| | found: | C 59.65 | H 5.25 | Cl 11.65 | N 23.15 |

MS m/z 301

NMR δ ppm (DMSO-$d_3$): 1.70 (m, 4H), 2.6–2.9 (m, 4H), 7.0–7.3 (m, 3H), 8.46, 8.62 (two s, 2H), 10.9 (bs, 1H).

According to the above described procedure the following compounds can be prepared:
$N^6$-(3-bromo-1-tetralyl) adenine hydrochloride;
$N^6$-(5-indanyl) adenine hydrochloride;
$N^6$-(7-bromo-5-indanyl) adenine hydrochloride;
$N^6$-(2-oxindol-5-yl) adenine hydrochloride:

| $C_{13}H_{11}ClN_6O$ | calcd: | C 51.58 | H 3.66 | Cl 11.71 | N 27.76 |
|---|---|---|---|---|---|
| | found: | C 51.50 | H 3.51 | Cl 11.55 | N 27.45 |

MS m/z 302

NMR δ ppm (DMSO-$d_3$): 3.53 (s, 2H), 6.86 (d, J=8.3 Hz, 1H) 6.52 (dd, J=2.2 and 8.3 Hz, 1H), 7.68 (d, J=2.2 Hz, 1H), 8.59, 8.62 (two s, 2H), 10.45 (s, 1H), 11.1 (bs, 1H);
$N^6$-(1-tetralylmethyl) adenine hydrochloride;
$N^6$-(5-indanylmethyl) adenine hydrochloride; and
$N^6$-(2-oxoindol-5-ylmethyl) adenine hydrochloride.

EXAMPLE 11

$N^6$-(1-tetralyl) adenine

A suspension of $N^6$-(1-tetralyl) adenine hydrochloride salt (3.018 g, 10 mM) and potassium carbonate (2.764 g, 20 mM) in methanol (60 ml) is stirred at ambient temperature for 0.5 h. The mixture is filtered and the filtrate evaporated under vacuum. The residue is purified by column chromatography using a 93:7 mixture of dichloromethane/methanol as eluant to give pure title compound in 90% yield.

| $C_{15}H_{15}N_5$ | calcd: | C 67.91 | H 5.70 | N 26.39 |
|---|---|---|---|---|
| | found: | C 67.65 | H 5.61 | N 26.25 |

MS m/z 265

By proceeding analogously the following compounds can be prepared:
$N^6$-(3-bromo-1-tetralyl) adenine;
$N^6$-(5-indanyl) adenine;
$N^6$-(7-bromo-5-indanyl) adenine;
$N^6$-(2-oxindol-5-yl) adenine;
$N^6$-(1-tetralylmethyl) adenine;
$N^6$-(5-indanylmethyl) adenine; and
$N^6$-(2-oxoindol-5-ylmethyl) adenine.

EXAMPLE 12

6-(1-tetralyloxy)-purine

To a solution of 1-hydroxytetralin (1.482 g, 10 mM) in 80 ml of aqueous potassium hydroxide solution containing 1.683 g (30 mM) of solid potassium hydroxide is added 6-chloropurine (1.546 g, 10 mM). The reaction mixture is stirred for about 0.5 h at room temperature until most of the 6-chloropurine dissolves and then heated on the steam bath for further 0.5 h. The mixture is cooled, filtered and the residue recrystallized from hot aqueous ethanol to give pure title compound in 60% yield.

| $C_{15}H_{14}N_4O$ | calcd: | C 67.65 | H 5.30 | N 21.04 |
|---|---|---|---|---|
| | found: | C 67.55 | H 5.25 | N 20.95 |

MS m/z 266

According to the above described procedure the following compounds can be prepared:
6-(3-bromo-1-tetralyloxy)-purine;
6-(5-indanyloxy)-purine;
6-(7-bromo-5-indanyloxy)-purine;
6-(2-oxindol-5-yloxy)-purine;
6-(1-tetralylmethoxy)-purine;
6-(5-indanylmethoxy)-purine; and
6-(2-oxindol-5-ylmethoxy)-purine.

EXAMPLE 13

6-(1-tetralylthio)-purine

To a solution of 6-chloropurine (1.546 g, 10 mM) in methanol (30 ml) is added a solution of 1-mercaptotetralin (4.929 g, 30 mM) in methanolic potassium hydroxide (60 ml containing 1.608 g (30 mM) solid potassium hydroxide). The reaction mixture is stirred for 0.5 h at room temperature and then boiled for 0.5 h at reflux. The solution is concentrated under vacuum and then cooled to give crystalline title compound in about 60% yield.

| $C_{15}H_{14}N_4S$ | calcd: | C 63.81 | H 5.00 | N 19.84 | S 11.35 |
|---|---|---|---|---|---|
| | found: | C 63.65 | H 4.95 | N 19.75 | S 11.30 |

MS m/z 282

By proceeding analogously the following compounds can be prepared:
6-(3-bromo-1-tetralylthio)-purine;
6-(5-indanylthio)-purine;
6-(7-bromo-5-indanylthio)-purine;
6-(2-oxoindol-5-ylthio)-purine;
6-(1-tetralylmethylthio)-purine;
6-(5-indanylmethylthio)-purine; and
6-(2-oxoindol-5-ylmethylthio)-purine.

EXAMPLE 14

6-(1-tetralylmethyl)-purine

A solution of 4,5-diamino-6-(1-tetralylmethyl)-pyrimidine sulfate (3.523 g, 10 mM) in formamide (30 ml) is heated to reflux for 0.5 h. The mixture is cooled, diluted with water and neutralized with aqueous sodium carbonate. The precipitate is removed by filtration and recrystallized from aqueous ethanol to yield pure title compound in about 70 % yield.

| $C_{16}H_{16}N_4$ | calcd: | C 72.70 | H 6.10 | N 21.20 |
|---|---|---|---|---|
| | found: | C 72.55 | H 6.05 | N 21.05 |

Ms m/z 264

By proceeding analogously the following compounds can be prepared:
10 6-(3-bromo-1-tetralylmethyl)-purine;
6-(5-indanylmethyl)-purine;
6-(7-bromo-5-indanylmethyl)-purine; and
6-(2-oxindol-5-ylmethyl)-purine.

EXAMPLE 15

$N^6$-(1-tetralyl) adenine

A suspension of 6-(1-tetralylthio)-purine(2.82 g, 10 mM) and 1-aminotetralin (4.416 g, 30 mM) in water (100 ml) is heated in a sealed tube at 130° C. for 20 h. Then the water is evaporated under vacuum and the residue chromatographed on silica gel by using dichloromethane/methanol mixtures as eluant. Thus almost pure title compound is obtained in about 40% yield.

| $C_{15}H_{15}N_5$ | calcd: | C 67.91 | H 5.70 | N 26.39 |
|---|---|---|---|---|
| | found: | C 67.85 | H 5.45 | N 26.35 |

MS m/z 265

By proceeding analogously the following compounds can be prepared:
$N^6$-(3-bromo-1-tetralyl) adenine;
$N^6$-(5-indanyl) adenine;
$N^6$-(7-bromo-5-indanyl) adenine;
$N^6$-(2-oxindol-5-yl) adenine;
$N^6$-(1-tetralylmethyl) adenine;
$N^6$-(5-indanylmethyl) adenine; and
$N^6$-(2-oxoindol-5-ylmethyl) adenine.

EXAMPLE 16

9-benzyl-$N^6$-(1-tetralyl)-adenine

A solution of $N^6$-(1-tetralyl) adenine (2.65 g, 10 mM) and benzylchloride (2.53 g, 20 mM) in dimethyl acetamide (DMAA, 100 ml) containing dry potassium carbonate (1.382 g, 10 mM) in suspension is heated with stirring for 16 h at 110° C. After filtration the solution is evaporated to dryness in vacuum and the residue is crystallized from ethanol to give pure title compound in about 50% yield.

| $C_{22}H_{21}N_5$ | calcd: | C 74.34 | H 5.96 | N 19.70 |
|---|---|---|---|---|
| | found: | C 74.21 | H 5.85 | N 19.55 |

MS m/z 355

EXAMPLE 17

9-ethyl-6-chloropurine

To a solution of 6-chloropurine (1.545 g, 10 mM) and iodoethane (3.22 g, 20 mM) in DMSO (50 ml) is added potassium carbonate (1.382 g, 10 mM). The resulting suspension is stirred for 2 h at room temperature, then diluted with water and extracted 3 times with ether. The ether extract is evaporated and the residue is purified by column chromatography using dichloromethane/ethanol 95:5 as eluant.

Thus pure title compound is obtained in about 50% yield.

| $C_5H_7ClN_4$ | calcd: | C 37.87 | H 4.45 | Cl 22.35 | N 35.33 |
|---|---|---|---|---|---|
| | found: | C 37.75 | H 4.35 | Cl 22.21 | N 35.30 |

MS m/z 158

EXAMPLE 18

Tablets each weighing 0.150 g and containing 25 mg of the active substance, can be manufactured as follows:
Composition (for 10,000 tablets):

| $N^6$-(1-tetralyl) adenine | 250 g |
|---|---|
| Lactose | 800 g |
| Corn starch | 415 g |
| Talc powder | 30 g |
| Magnesium stearate | 5 g |

The $N^6$-(1-tetralyl) adenine, the lactose and half of the corn starch are mixed; the mixture is then forced through a sieve of 0.5 mm mesh size. Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate is added, carefully mixed and processed into tablets.

EXAMPLE 19

Capsules, each dosed at 0.200 g and containing 20 mg of the active substance can be prepared.
Composition for 500 capsules:

| $N^6$-(5-indanyl) adenine | 10 g |
|---|---|
| Lactose | 80 g |
| Corn starch | 5 g |
| Magnesium stearate | 5 g |

This formulation is encapsulated in two-piece hard gelatin capsules and dosed at 0.200 g for each capsule.

EXAMPLE 20

Tablets each weighing 0.150 g and containing 25 mg of the active substance, can be manufactured as follows:
Composition (for 10,000 tablets):

| 4-(5-indanylamino)-pyrido[2,3-d]pyrimidine | 250 g |
|---|---|
| Lactose | 800 g |
| Corn starch | 415 g |
| Talc powder | 30 g |
| Magnesium stearate | 5 g |

The 4-(5-indanylamino)-pyrido[2,3-d]pyrimidine, the lactose and half of the corn starch are mixed; the mixture is then forced through a sieve of 0.5 mm mesh size. Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate is added, carefully mixed and processed into tablets.

EXAMPLE 21

Capsules, each dosed at 0.200 g and containing 20 mg of the active substance can be prepared.
Composition for 500 capsules:

| 4-(1-tetralylamino)-pyrido[2,3-d]pyrimidine | 10 g |
|---|---|
| Lactose | 80 g |
| Corn starch | 5 g |
| Magnesium stearate | 5 g |

This formulation is encapsulated in two-piece hard gelatin capsules and dosed at 0.200 g for each capsule.

We claim:
1. A bicyclic condensed pyrimidine compound having the following general formula (I)

(I)

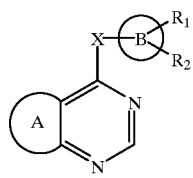

wherein

X is —CH$_2$—, —NH—(CH$_2$)$_n$—, —O—(CH$_2$)$_n$— or —S—(CH$_2$)$_n$— in which n is zero or 1;

A is a 4,5-fused imidazole ring N-substituted by R$_3$ which is hydrogen, C$_1$-C$_4$ alkyl or benzyl;

B is a 2-oxindole ring;

each of R$_1$ and R$_2$, independently, is hydrogen, C$_1$-C$_4$ alkyl, halogen, hydroxy, C$_1$-C$_4$ alkoxy, C$_1$-C$_4$ alkoxycarbonyl, nitro, cyano or CF$_3$;

or pharmaceutically acceptable salts thereof.

2. A compound of formula (I), according to claim 1, wherein X, A and B are as defined in claim 1, R$_1$ is hydrogen or halogen, and R$_2$ and R$_3$ are H; or pharmaceutically acceptable salts thereof.

3. The bicyclic condensed pyrimidine compound according to claim 1, wherein said compound is N$^6$-(2-oxindol-5-yl)adenine.

4. A compound selected from the group consisting of N$^6$-(2-oxindol-5-yl) adenine; N$^6$-(2-oxindol-5-ylmethyl) adenine; 6-(2-oxindol-5-yloxy)-purine; 6-(2-oxindo 5-ylthio)-purine; 6-(2-oxindol-5-ylmethyl)-purine; 6-(2-oxindol-5-ylmethoxy)-purine; and 6-(2-oxindol-5-ylmethylthio)-purine.

5. A pharmaceutical composition comprising a compound of formula (I), as defined in claim 1, or a pharmaceutically salt thereof, as an active principle, and a pharmaceutically acceptable excipient.

6. A process for the preparation of a bicyclic pyrimidine compound of formula (I)

(I)

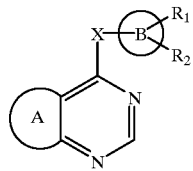

wherein

X is —CH$_2$—, —NH—(CH$_2$)$_n$—, —O—(CH$_2$)$_n$— or —S—(CH$_2$)$_n$— in which n is zero or 1;

A is a 4,5-fused imidazole ring N-substituted by R$_3$ which is hydrogen, C$_1$-C$_4$ alkyl or benzyl;

B is a 2-oxindole ring;

R$_1$ and R$_2$ are independently hydrogen, C$_1$-C$_4$ alkyl, halogen, hydroxy, C$_1$-C$_4$ alkoxy, C$_1$-C$_4$ alkoxy carbonyl, nitro, cyano or CF$_3$; or pharmaceutically acceptable salts thereof; the process comprising;

a) reacting a compound of formula (II)

(II)

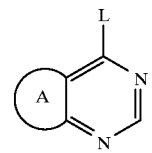

wherein A is as defined above and L is a leaving group, with an amine compound of formula (III)

(III)

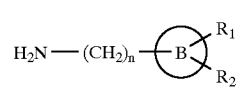

wherein n, B, R$_1$ and R$_2$ are as defined above thus obtaining a compound of formula (I) in which X is —NH—(CH$_2$)$_n$—;or b) reacting a compound of formula (II) as defined above, with an hydroxy compound of formula (IV)

(IV)

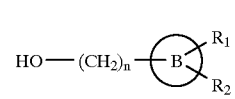

wherein n, B, R$_1$ and R$_2$ are as defined above thus obtaining a compound of formula (I) in which X is —O—(CH$_2$)$_n$—; or c) reacting a compound of formula (II) as defined above, with a thio compound of formula (V)

(V)

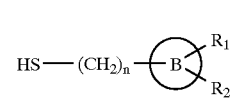

wherein n, B, R$_1$ and R$_2$ are as defined above, thus giving a compound of formula (I) in which X is —S—(CH$_2$)$_n$—; or d) reacting a compound of formula (VI)

(VI)

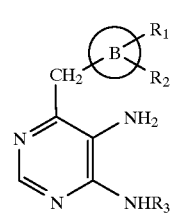

wherein B, R$_1$ and R$_2$ and R$_3$ are as defined above, with formamide (HCONH$_2$), thus providing a compound of formula (I) wherein X is —CH$_2$—.

7. The process of claim 6, wherein the product is N$^6$-(2-oxindol-5-yl) adenine.

* * * * *